(12) United States Patent
Lupin et al.

(10) Patent No.: US 8,114,905 B2
(45) Date of Patent: *Feb. 14, 2012

(54) COMPACTED 2,2-DIBROMO-3-NITRILOPROPIONAMIDE

(75) Inventors: Michael Lupin, Haifa (IL); Ayala Lupin, legal representative, Haifa (IL); David Feldman, Haifa (IL)

(73) Assignee: Bromine Compounds Limited, Beer-Sheva (IL)

( * ) Notice: Subject to any disclaimer, the term of this patent is extended or adjusted under 35 U.S.C. 154(b) by 392 days.

This patent is subject to a terminal disclaimer.

(21) Appl. No.: 12/381,904

(22) Filed: Mar. 17, 2009

(65) Prior Publication Data

US 2009/0202603 A1 Aug. 13, 2009

Related U.S. Application Data

(63) Continuation of application No. 10/381,527, filed as application No. PCT/IL01/00911 on Sep. 26, 2001, now Pat. No. 7,524,884.

(30) Foreign Application Priority Data

Sep. 28, 2000 (IL) .......................................... 138771

(51) Int. Cl.
*A01N 37/34* (2006.01)
*A01N 43/30* (2006.01)

(52) U.S. Cl. ...................................... 514/528; 514/464

(58) Field of Classification Search .................... 514/528
See application file for complete search history.

(56) References Cited

U.S. PATENT DOCUMENTS

| | | | |
|---|---|---|---|
| 3,928,575 A | 12/1975 | Moyle et al. | |
| 4,528,125 A | 7/1985 | Alderman et al. | |
| 4,554,367 A | 11/1985 | Wehner et al. | |
| 4,678,516 A | 7/1987 | Alderman et al. | |
| 4,695,464 A | 9/1987 | Alderman | |
| 4,800,082 A | 1/1989 | Karbowski et al. | |
| 4,849,415 A | 7/1989 | Zweigle | |
| 6,034,081 A | 3/2000 | Whittemore et al. | |
| 6,500,444 B1 | 12/2002 | Ferenc et al. | |
| 6,685,840 B2 | 2/2004 | Hatch | |
| 7,524,884 B2 * | 4/2009 | Lupin et al. ................. | 514/528 |

FOREIGN PATENT DOCUMENTS

| | | |
|---|---|---|
| EP | 0 285 209 B1 | 10/1988 |
| EP | 0 953 284 A1 | 11/1999 |
| EP | 0 954 966 A1 | 11/1999 |
| ES | 8 605 221 A1 | 8/1986 |
| WO | WO-98/25458 A1 | 6/1998 |
| WO | WO-99/18162 A1 | 4/1999 |

* cited by examiner

*Primary Examiner* — Jake M. Vu
(74) *Attorney, Agent, or Firm* — Roach Brown McCarthy & Gruber, P.C.; Kevin D. McCarthy

(57) ABSTRACT

The present invention provides an essentially pure compacted 2,2-Dibromo-3-nitrilopropionamide (DBNPA) in a granular and/or tablet and/or briquette and/or pellet form. The present invention further provides a process for preparing the same essentially pure compacted DBNPA.

11 Claims, No Drawings

COMPACTED 2,2-DIBROMO-3-NITRILOPROPIONAMIDE

CROSS-REFERENCE TO RELATED APPLICATIONS

This application is a continuation of U.S. application Ser. No. 10/381,527, filed Oct. 6, 2003, which is a national stage application of International Application No. PCT/IL01/00911, filed Sep. 26, 2001, which claims priority from Israeli Application No. 138771 filed Sep. 28, 2000, the disclosures of which are hereby incorporated by reference herein.

FIELD OF THE INVENTION

The present invention relates to compacted forms of 2,2-Dibromo-3-nitrilopropionamide (DBNPA), namely a granular and/or a tablet and/or a briquette and/or a pellet form that each has distinguished commercial and technological advantages over same material in the known powder form.

BACKGROUND OF THE INVENTION 2,2-Dibromo-3-nitrilopropionamide (DBNPA) is a biocide which is used in industrial water treatment, cooling systems and paper mills. DBNPA is an efficient biocide with a rapid microbiocidal broad-spectrum activity, especially in water systems that contain high organic loads.

The main current application of DBNPA is as a liquid formulation, which contains a mixture of water and an organic solvent such as a glycol (for example, polyethylene glycol (PEG), dipropylene glycol (DPG), ethylene glycol, etc.) and others. The active ingredient (DBNPA) is only 5-25% of such liquid formulation. The addition of an organic solvent is required for dissolution of the relatively water-insoluble DBNPA into a liquid formulation.

Prior art teaches the production of DBNPA as a powdered material which can be used for the preparation of a liquid or solid formulation.

Several types of sustained-release compositions containing DBNPA have been described:

1) EP 285 209 recites a solid sustained release antimicrobial composition (in a tablet form), comprising 1 to 90% by wt of a halogenated amide (including DBNPA) antimicrobial agent, 10 to 80% by wt of a hydrophilic polymer, 0 to 80% by wt of a compression agent and 0 to 10% by wt of a mold release agent. A composition comprising 40% DBNPA, 30% Methocel (water soluble cellulose polymer), 27% $CaHPO_4$ (as compressing agent) and 3% stearic acid, was specifically demonstrated.
2) WO 98/25458 discloses a solid sustained-release tablet consisting of DBNPA admixed with a water-soluble natural or synthetic polymer. Besides the addition of a synthetic polymer into the formulation, the tablet is coated with an additional water-soluble cellulosic polymer.
3) WO 99/18162 discloses a biocidal powder coating composition comprising thermoplastic and/or thermosetting resins based on epoxy, polyester, acrylic or polyurethane resins. The biocide used is a liquid bio-active material (including DBNPA) and/or specially selected solid bioactive materials (for example, solid thiazine-thiones, thiolphthalimides, and others). The biocides are homogeneously mixed or bonded with the particles of the powder. The process of preparing said biocidal powder coating composition is characterized by blending the components of the powder coating composition in a premixer, followed by feeding the mixture into an extruder, heating to a temperature high enough to melt and mix most of the major components, and cooling to a solid form.
4) EP 953 284 discloses a composition (in a tablet form) for delivering the DBNPA biocide to an oil field fracturing fluid, comprising effervescing agents such as sodium bicarbonate, citric acid and borax. The composition comprises about 35-65% DBNPA, about 15-28% sodium carbonate, 15-27% citric acid and up to about 20% borax.
5) EP 954 966 recites controlled release compositions comprising a biologically active compound, including DBNPA, and a hydroxystyrene polymer (e.g. hydroxystyrene homopolymer, methylhydroxystyrene homopolymer, halohydroxystyrene homopolymer and their copolymers). The weight ratio of DBNPA to the polymer is from 0.1:99.9 to 95:5.

The above prior art is related to sustained-release formulations (including in a tablet form) which contain various additives, such as polymeric matrix, binders and compression agents in significant amount. However, no free DBNPA compound in a compacted form has been used and/or described in the literature. The ability to provide an almost net content of the active compacted material (such as in a tablet, granule, pellet or briquette form) is most certainly a significant advantage.

The handling of the existing DBNPA powdered solid material requires severe safety precautions due to the hazardous nature of this biocide, especially in a fine powdered form.

An additional problem concerning the application of powdered DBNPA, is the tendency of the powder to agglomerate, creating lumps and a bulky material. This phenomenon reduces the flowability of the product and causes handling and safety problems.

In view of these disadvantages of powdered DBNPA there is a need for a safer, easy to handle and user-friendly densified particulate DBNPA. Such DBNPA should be free of said agglomeration phenomena. As was mentioned above, the densified forms known in the art have the considerable drawback of requiring the addition of binders and fillers to obtain suitable solid forms of the biocide. Therefore, compacted forms known in the art do not provide net or almost net contents of active material in the tablet, granule, briquette or pellet form. It has now been found that it is possible to prepare compacted forms of DBNPA which have sufficient strength and provide a slow release of the active material into the water without losing their compacted nature. It has further been surprisingly found that it is possible to prepare compacted forms of this biocide, without employing any binder or filler.

It is an object of the present invention to provide a compacted DBNPA particle in a granular and/or a tablet and/or a briquette and/or a pellet form. It is a further object of the present invention to provide a compacted DBNPA particle having a diameter larger than 0.5 mm., with no binder, filler or additive added. Yet a further object of the present invention is to provide a compacted DBNPA particle that contains from 0 to about 3 wt % of water content. It is yet another object of the present invention to provide a non-agglomerative DBNPA.

SUMMARY OF THE INVENTION

The present invention provides an essentially pure compacted 2,2-Dibromo-3-nitrilopropionamide (DBNPA) in a granular and/or tablet and/or briquette and/or pellet form. A process for producing the same essentially pure compacted DBNPA is provided, as well.

DESCRIPTION OF THE PREFERRED EMBODIMENTS

A major embodiment of the present invention is to provide a process for obtaining dry-compacted DBNPA in either granular and/or tablet and/or briquette and/or pellet form. It should be pointed out, however, that as it is apparent to a person skilled in the art, the actual shape of the compacted or densified form is not an important parameter, and any obtainable shape is within the scope of the present invention.

The compacted DBNPA particle of the present invention avoids the above mentioned shortcomings of powdered DBNPA and offers a safer material, easy to handle, user friendly and at the same time meets the highly demanding environmental requirements existing for any mode of biocide application. The compacted DBNPA can be used to prepare a liquid formulation with various solvents or to generate a fresh aqueous biocide solution on site.

The application of the compacted DBNPA, according to the present invention has several advantages:
a) Use of a concentrated solid biocide (>95 wt % active material), and the avoidance of an organic solvent which is required as a co-solvent to prepare an aqueous formulation.
b) Simplification of operation and minimization of handling, resulted in less exposure of the user to the harmful biocide.
c) Increased logistic efficiency and minimization of environmental pollution.

According to the invention, it has been found that powdered DBNPA (such as 98 wt % active material) can be compacted in a dry-process, without the addition of a binder, to yield a product in either a tablet and/or a granular and/or a briquette and/or a pellet form.

According to the invention, the process for compacting powdered DBNPA provides high quality tablets at a moderate pressure of 1300 kg/cm$^2$. More specifically, the process is characterized in that DBNPA is compressed with a pressure of at least 500 kg/cm$^2$, to yield a compacted DBNPA pellet or tablet. Preferably, the pressure employed is between about 1000 and 2000 kg/cm$^2$. Thus, for instance, the density obtained under a compaction pressure of 1500 kg/cm$^2$ (2.1 g/cm$^3$) is 88% of the theoretical density of DBNPA.

Preferred compacted biocidal products of the present invention, are those comprising at least 97% (by wt) DBNPA, and between 0 and about 3% (by wt) of water and/or inert ingredient.

The following examples are provided merely to illustrate the invention and are not intended to limit the scope of the invention in any manner.

EXAMPLES

1. Preparation of DBNPA Pellets

Powdered DBNPA was dried and compacted using an hydraulic press, under three different pressure levels: 500, 1000 and 1500 kg/cm$^2$, using a tungsten carbide cylindrical mold 1.8 cm in diameter. The compaction was effected using dry powder and a powder which was humidified by the addition of 2 wt % H$_2$O. The ratio of the cylindrical pellet height/diameter is about 1.

Each pellet was tested to determine its density and Crushing Strength (CS). The density of the compact was determined by measuring its dimensions and weight. CS was measured by standard compression test. Samples that were humidified by the addition of 2 wt % H$_2$O were dried at 105° C. for 2 hours before the density and CS were measured. The results of these tests are shown in Table 1. The CS of compacted DBNPA which still contained 2 wt % H$_2$O was 28, 44 and 70 kg/cm$^2$ for the compaction pressures of 500, 1000 and 1500 kg/cm$^2$ respectively.

TABLE 1

| Compaction pressure kg/cm$^2$ | Dry Compacted DBNPA | | Dry Compacted DBNPA with 2 wt % water | |
|---|---|---|---|---|
| | Density g/cm$^3$ | CS kg/cm$^2$ | Density g/cm$^3$ | CS kg/cm$^2$ |
| 500 | 1.8 | 31 | 1.9 | 18 |
| 1000 | 1.9 | 37 | 2.1 | 25 |
| 1500 | 2.1 | 45 | 2.12 | 35 |

2. Process for Tableting Powdered DBNPA (Laboratory Scale)

Powder containing at least 98 wt % 2,2-Dibromo-3-nitrilopropionamide (DBNPA) was weighed into separate portions of about 3 g each, and the portions were tableted individually in a hydraulic press with a single action die. The die had a diameter of 18 mm and the pressure applied was 500 psi equivalent to 1300 kg/cm$^2$. The tablets were sealed in individual polyethylene bags for further measurements.

The tablets were weighed and their thickness measured for calculation of their density. The crushing strength was determined in the diametral mode with a Chatillon Digital Force Gauge (DFG-50), with a maximum force of 25 kg. A total of 40 tablets were measured and the averages of the determinations are given in Table 2.

TABLE 2

Physical Properties of the DBNPA Tablets

| | |
|---|---|
| Weight, g | 3.01 ± 0.45 |
| Thickness, mm | 5.67 ± 0.86 |
| Density, g/cm$^3$ | 2.09 ± 0.15 |
| Crushing strength, kg/cm$^2$ | 10.15 ± 2.74 |

The static dissolution rate of the DBNPA tablets was determined to be 0.15 gr/h±0.04, by the "weight loss of solid method."

3. Process for Tableting Powdered DBNPA (Scaling-Up)

A scale-up of the laboratory tableting process was performed in the equipment of a tableter manufacturer, in which 200 kg of tablets were produced from powder containing at least 98 wt % DBNPA.

The tableting process was performed using a rotary, multi-die tableter, die diameter 14 mm, with automatic feeding system. No problems were observed with filling up to 250-300 tabs/min. Specific compression force 1500 to 2000 kg/cm$^2$.

The DBNPA tablets obtained from the scale-up process were examined and compared to the ones obtained in the laboratory-scale process (Table 3).

TABLE 3

Physical Properties of the DBNPA Tablets

| Tablets | Weight, g | Thickness, mm | Diameter, mm | Density, g/cm$^3$ | Crushing Strength, kg/cm$^2$ |
|---|---|---|---|---|---|
| Scale-up | 3.05 ± 0.16 | 9.98 ± 0.11 | 14.2 | 1.93 ± 0.09 | 11.6 ± 3.1 |
| Lab. | 3.00 ± 0.45 | 5.67 ± 0.86 | 18 | 2.09 ± 0.15 | 10.2 ± 2.8 |

The tablets produced during the scale-up process had a smaller diameter and a greater thickness than those produced at the laboratory-scale, but the average weight was the same. The density of the tablets from the scale-up was slightly lower, but the crushing strength was 10% higher. The static dissolution rate of the DBNPA tablets was determined to be 0.14±0.03 gr/h, by the "weight loss of solid method". This result is very similar to the dissolution rate that was measured for the tablets that were prepared in the laboratory (0.15±0.04 gr/h).

4. Process for Granulating Powdered DBNPA (Compaction/Granulation)

Production of granular DBNPA by the compaction/granulation process was performed using a small WP 50 laboratory compactor, with a single 5 mm screen installed in the crushing system. Powder containing at least 98 wt % DBNPA was used. The compaction of the powder to a flake and subsequent crushing to ~5 mm granules went smoothly, and the material was screened. 11.5 kg of 2-5 mm granules were produced. The feed rate was 110 kg/hr. The DBNPA compacted well, without the aid of a binder, and high quality granules were obtained.

The invention claimed is:

1. A non-agglomerative compacted 2,2-dibromo-3-nitrilopropionamide (DBNPA) in a form selected from the group consisting of granular form, tablets, briquettes, and pellets, free from added binders, additives, and fillers, consisting essentially of
   at least 97 wt % of DBNPA and the balance is water and inert ingredients, wherein said compacted DBNPA was compressed in a compactor.

2. The non-agglomerative compacted granular DBNPA, according to claim 1, consisting of granules having a diameter larger than 0.5 mm.

3. The non-agglomerative compacted DBNPA, according to claim 1, providing a release of DBNPA into water without losing the compacted nature.

4. The non-agglomerative compacted DBNPA according to claim 1, comprising at least 98% of DBNPA.

5. The non-agglomerative compacted granular DBNPA according to claim 2, consisting of granules having a diameter of at least 2 mm.

6. The non-agglomerative compacted DBNPA according to claim 1, wherein said DBNPA is in a tablet form which has been compressed with a pressure of at least 500 kg/cm$^2$.

7. A process for producing the non-agglomerative compacted DBNPA of claim 1, including the step of converting powdered DBNPA into said compacted DBNPA without the addition of binders and/or fillers.

8. The process for producing compacted tableted DBNPA, according to claim 7, including the step of converting powdered DBNPA into tableted DBNPA.

9. The process for producing compacted granular DBNPA, according to claim 7, including the step of converting powdered DBNPA into granular DBNPA.

10. The process for producing compacted tableted DBNPA, according to claim 7, characterized in that DBNPA is compressed with a pressure of at least 500 kg/cm$^2$, to yield a compacted DBNPA product.

11. The process according to claim 10, wherein the pressure is between about 1000 and 2000 kg/cm$^2$.

* * * * *